United States Patent [19]

Hedberg et al.

[11] Patent Number: 4,550,210

[45] Date of Patent: Oct. 29, 1985

[54] PROCESS FOR PREPARING HALOGEN-TERMINATED OLIGOMERS USEFUL IN THE PRODUCTION OF ACETYLENE-TERMINATED RESINS

[75] Inventors: Frederick L. Hedberg, Xenia; Marilyn R. Unroe, Dayton, both of Ohio

[73] Assignee: The University of Dayton, Dayton, Ohio

[21] Appl. No.: 522,940

[22] Filed: Aug. 12, 1983

[51] Int. Cl.[4] .................. C07C 147/10; C07C 147/12
[52] U.S. Cl. ...................................... 568/33; 568/641
[58] Field of Search ................................. 568/33, 641

[56] References Cited

U.S. PATENT DOCUMENTS 4,070,383  1/1978  Rutledge ........................ 260/396 N
4,356,325  10/1982  Harrison et al. ..................... 568/33

FOREIGN PATENT DOCUMENTS 1911799  9/1970  Fed. Rep. of Germany ........ 568/58

OTHER PUBLICATIONS

Sabourin, The Synthesis of Polymer Precursors and Exploratory Research Based on Acetylene Displacement Reaction, 10, 1980.
Harrison et al., Low Cost Routes to Acetylenic Intermediates, Dec. 1979.
Bacon et al., "Metal Ions and Complexes in Organic Reactions, Part IV, Copper-Promoted Preparations of Diaryl Ethers & Competing Hydrogen-Transfer Processes", J. Chem. Soc., 4953 (1965).

*Primary Examiner*—Donald G. Daus
*Assistant Examiner*—Cecilia Shen
*Attorney, Agent, or Firm*—Biebel, French & Nauman

[57] ABSTRACT

A process for preparing halogen-terminated oligomers by an Ullmann condensation is disclosed wherein a diphenol and a dihalobenzene are reacted in the presence of cuprous oxide in 2,4,6-collidine. The oligomers are useful in producing acetylene-terminated resins by replacing the terminal halogen atoms with acetylene groups.

6 Claims, No Drawings

PROCESS FOR PREPARING HALOGEN-TERMINATED OLIGOMERS USEFUL IN THE PRODUCTION OF ACETYLENE-TERMINATED RESINS

BACKGROUND OF THE INVENTION

The present invention relates to a cost effective process for producing acetylene-terminated resins from halogen-terminated oligomers prepared by an Ullmann condensation in 2,4,6-collidine with an excess of cuprous oxide.

Acetylene terminated resins are being considered as substitutes for epoxy resins in certain composites because they exhibit better resistance to moisture than their epoxy counterparts. One drawback of these resins, however, is that they have been relatively difficult to synthesize and expensive to produce. Using prior synthetic approaches it has been difficult to control the average oligomer length in order to maintain a reproducible and acceptable balance between processability and mechanical properties. In addition total product yields have been difficult to reproduce and maximize. Consequently, prior syntheses have not been entirely satisfactory for producing these oligomers on a commercial scale.

The preparation of acetylene-terminated sulphones by an Ullman-type condensation is described in U.S. Pat. No. 4,356,325 to Harrison et al (1982). There, a sulfonyldiphenol, such as 4,4'-sulfonyldiphenol, is reacted with meta- or para-dibromobenzene in the presence of a potassium base, a copper salt, and a pyridine solvent to produce a bromine-terminated oligomer which is converted to the acetylene-terminated oligomer by reacting with a substituted terminal acetylene compound. This synthesis has not been entirely satisfactory, however, because the yield of the bromine-terminated oligomers is low and the oligomer chain length cannot be adequately controlled by varying the mole ratio of the sulfonyldiphenol to the dibromobenzene. Consequently, it is difficult to obtain oligomers having predetermined processing characteristics and mechanical properties by this synthesis R. Bacon and G. Stewart, "Metal Ions and Complexes in Organic Reactions, Part IV, Copper-promoted Preparation of Diaryl Ethers and Competing Hydrogen-transfer Processes", *J. Chem. Soc.*, 4953 (1965) discloses the use of cuprous oxide in combination with 2,4,6-collidine in the condensations of phenols (including a diphenol) and monobrominated aromatic compounds to produce aryl ethers. However, the paper notes a competing reaction in which bromine is replaced by hydrogen in the reactants which, on its face, would discourage using the subject catalyst-solvent system to produce oligomers in which terminal bromine atoms are required. Furthermore, the paper does not address the synthesis of oligomers by using dibromo compounds in the reaction, in which other catalyst solvent systems have failed to provide reproducible results and high yields.

Thus, there is a need for a commercially suitable process for producing halogen-terminated oligomers for use in forming acetylene terminated oligomers which provides a means for tailoring the chain length of the oligomers and providing the oligomers in high yields.

SUMMARY OF THE INVENTION

In accordance with the present invention, halogen-terminated terminated oligomers useful in the production of acetylene-terminated oligomers are prepared by Ullmann condensation using 2,4,6-collidine, as a solvent, and an excess of cuprous oxide as a catalyst-reagent. The reaction proceeds as follows:

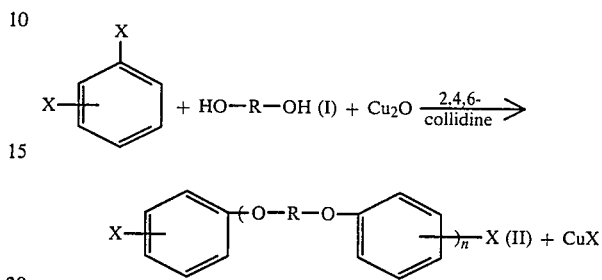

where X is a halogen atom (e.g., fluorine, chlorine, bromine or iodine), n is an integer (typically less than 3), and $R^1$ is defined below. It has been found that this reaction, in contrast to Ullmann-type condensations using other catalyst-solvent systems and the system taught in U.S. Pat. No. 4,356,325, enables one to tailor the chain length of the oligomer by varying the ratio of the diphenol and the dihalobenzene and provides halogen-terminated oligomers in high yields. Thus, this reaction affords a means of obtaining a balance between toughness, processability and use temperature in the oligomers.

The process of the present invention is particularly useful in producing the following bromine-terminated oligomers
4,4'-bis(3-bromophenoxy)phenylsulfone;
4,4'-bis(4-bromophenoxy)phenylsulfone;
2,2'-bis[4-(3-bromophenoxy)phenyl]propane;
2,2'-bis[4-(4-bromophenoxy)phenyl]propane;
1,3-bis(3-bromophenoxy)benzene;
4,4'-bis(3-bromophenoxy)phenylsulfide;
4,4'-bis(4-bromophenoxy)phenylsulfide; etc.

Thus, in one embodiment the present invention provides a process for producing halogen-terminated oligomers useful in the production of acetylene-terminated oligomers which comprises reacting an aromatic diphenol or bisphenol with a dihalobenzene compound in the presence of at least a stoichiometric amount of cuprous oxide in an Ullmann-type condensation in 2,4,6-collidine.

Another embodiment relates to the production of acetylene terminated oligomers which are prepared from bromine terminated oligomers prepared by the aforesaid process.

DETAILED DESCRIPTION OF THE INVENTION

In the preferred case the dihalobenzene used in the present invention is a meta- or para-substituted benzene and still more preferably 1,3- or 1,4-dibromobenzene. To avoid undesirable crystallizaton in the acetylene-terminated product, it is desirable to have some meta-dihalobenzene present. Dihalobenzenes containing 70 to 100% of the meta isomer and 0 to 30% of the para isomer are preferably used.

$R^1$ in the above formula (I) for the diphenol can be a mononuclear or dinuclear aromatic moiety where the aromatic moiety is most typically a phenyl group. For example, the diphenol can be a sulfonyldiphenol, an alkylenediphenol, a thiodiphenol, or a simple phenylene diphenol such as resorcinol. Representative examples of diphenols useful in the present invention include 4,4'-sulfonyldiphenol, 4,4'-isopropylidenediphenol, 4,4'-thiophenol, and resorcinol. The catalyst-solvent system used in the present invention can also be employed with such diphenols as 3,3'-sulfonyldiphenol, 3,4'-sulfonyldiphenol, 3,2'sulfonyldiphenol, 4,2'-sulfonyldiphenol, 3,3'-isopropylidenediphenol, 3,4'isopropylidenediphenol, 3,2'-isopropylidenediphenol, 4,2'-isopropylidenediphenol, 4,4'-methylenediphenol and the like.

The reaction can be conducted under any suitable reaction conditions. Suitable temperatures range from about 100° to 200° C. and more preferably from about 160 to 195° C. Typically the reaction is conducted at atmospheric pressure although pressures up to 250 psig could be used. Suitable reaction times are usually in the range of about 7 to 120 hours and optimumly from about 7 to 20 depending on the reactivity of the diphenol.

Cuprous oxide is used in at least a slight stoichiometric amount and, preferably in a slight excess, i.e., in a molar amount at least double the molar amount of the dihalobenzene employed. The rate of the reaction will vary inversely with the amount of 2,4,6-collidine employed. It has been found desirable to use the collidine in an amount approximately 2 to 20 times, and more preferably 5 to 10 times, the molar amount of diphenol to achieve a smooth, controlled, reaction between the diphenol and the dihalobenzene.

As pointed out above, the principal advantage of the process of the present invention is that it provides a reproducible means for controlling the chain length of the halogen-terminated oligomer. This is accomplished by varying the molar ratio of the dihalobenzene compound to the diphenol alone or in conjunction with other reaction conditions. The ratios used can vary over a broad range depending on the chain length that is desired and the nature of the monomers selected. Usually the ratio will vary from about 1.5:1 to 30:1 (dihalobenzene:diphenol). High ratios of dihalobenzene to diphenol (e.g., in excess of about 10:1) are used to achieve a high ratio of n=1 oligomer, i.e., oligomer of the above formula II wherein n=1. Ratios in excess of about 25:1 to 30:1 do not significantly increase the percentage of n=1 oligomer and, as such, are generally unnecessary. If higher amounts of n=1 oligomer are desired, it is recommended to concentrate the n=1 oligomer by distillation.

To increase chain length and improve toughness (at the expense of processability), the amount of n=1 oligomer is reduced by reducing the ratio of dihalobenzene to diphenol. Thus, depending on the nature of the specific dihalobenzene and diphenol used, the percentage of n=1 oligomer can be reduced by using a molar ratio of about 1.5:1 to 4:1 (dihalobenzene:diphenol) to produce oligomer compositions containing in the range of 30 to 60% n=1 oligomer. In preparing oligomers having lower n=1/n>1 ratios, a small amount of monobrominated oligomer is produced. This has not been found to be disadvantageous.

Halogen-terminated oligomers prepared in accordance with the present invention can be converted to acetylene-terminated oligomers in a conventional manner. A suitable conversion is described in U.S. Pat. No. 4,356,325, which is incorporated herein by reference, and involves reacting the brominated oligomer with a substituted terminal acetylene compound containing a hydroxyl group followed by removing the hydroxyl group from the oligomer. Useful substituted terminal acetylene compounds are compounds of the formula $$HC\equiv C-Z$$

wherein Z is $CR^2R^3OH$ wherein $R^2$ and $R^3$ can be the same or different and are selected from the group consisting of hydrogen, lower alkyl groups having from 1 to 4 atoms, phenyl, substituted phenyl; or where $R^2$ and $R^3$ together with the carbon atom to which they are attached form a saturated 5- or 6-membered ring. Suitable acetylenic compounds include the following: 3-methylbutyn-3-ol; 2-methyl-3-butyn-2-ol; 3-methyl-1-pentyn-3-ol; 3-ethyl-1-pentyn-3-ol; 2-phenyl-3-butyn-2-ol; 1-ethynylcyclohexanol; and 1-ethynylcyclopentanol.

Usually the halogen-terminated oligomer is reacted with the terminal acetylene compounds in a molar ratio of about 1:2, but suitable molar ratios include those from 1:0.5 to 1:100 and are more preferably from 1:2 to 1:5. Suitable solvents include but are not limited to dimethylamine, trimethylamine, diethylamine, triethylamine, ethylpropylamine, ethylbutylamine and dibutylamine. The catalyst employed is a complex palladium salt containing two halogen moieties, where the halogen is selected from the group consisting of bromine, iodine and chlorine, and two trisubstituted phosphine moieties where the constituents are selected from phenyl, alkyl groups having from one to 4 carbon atoms, and substituted phenyl groups. Representative examples of suitable complex palladium salts include bis(triphenylphosphine)palladium dichloride, bis(triphenylphosphine) palladium dibromine; bi(tripropylphosphine)palladium dichloride and the like. The reaction is normally carried out under mild conditions, e.g., 50 to 125° C. at atmospheric pressure. The reaction mixture is preferably subjected to a metals removal step for removal of palladium, copper and any other metal contaminants which can cause the oligomer to cure prematurely.

Base catalyzed cleavage of the hydroxyl group is conducted under any suitable reaction conditions, such as a temperature in the range of between about 70° and about 130° C., and preferably between about 90° and 120° C., in the presence of a suitable base, such as potassium hydroxide or sodium hydroxide for 0.5 to 10 hours, preferably 1 to 4 hours, for example. Potassium hydroxide is preferred.

The present invention will be illustrated in more detail by the following non-limiting examples.

EXAMPLE 1

Preparation of a 4,4'-bis(3-bromophenoxy) Phenylsulfone (BPDS) and its Oligomers (OBPDS)

To a 100 mL flask fitted with a reflux condenser, a nitrogen inlet, and a thermometer were added 4,4'-sulfonyldiphenol (SDP) (4.0 g, 16 mmole), $Cu_2O$ (4.61 g, 32 mmole), the appropriate molar amount of dibromobenzene (DBB) (95% 1,3-dibromobenzene and 5% 1,4-dibromobenzene) (see Table I), and 2,4,6-collidine (24.2 g, 100 mmole). The solution was magnetically stirred under an atmosphere of nitrogen for ten minutes before the application of heat. The flask was heated under nitrogen atmosphere at an internal temperature of 170° C. until TLC (thin layer chromatography) indicated no starting diphenol or monosubstituted phenol intermediate remained.

The solvents were stripped from the crude mixture by high vacuum rotary evaporation at 180° C., and the residue was then dissolved into minimal methylene chloride and poured into carbon tetrachloride. After refluxing off the $CH_2Cl_2$, the $CCl_4$ was hot filtered through diatomaceous earth packed into a coarse frit. The filtrate was then extracted with 12 N hydrochloric acid (2 ×50 mL) at 50° C. for ½ hour, cooled, and separated. After subsequent water washes (2×100 mL) the $CCl_4$ was extracted with 10% aqueous potassium hydroxide (2×50 mL), washed with water (4×100 mL), dried on anhydrous $MgSO_4$ and stripped to dryness by rotary evaporation to yield the crude BPDS/OBPDS product.

To determine the BPDS/OBPDS ratio, a 0.5 g sample of the crude product was chromatographed on a column packed with silica gel to separate the BPDS from the OBPDS. BPDS was eluted with 2:1 $CCl_4/CH_2Cl_2$, and OBPDS was eluted with $CH_2Cl_2$. Monomeric BPDS (n=1) was a white powder, m.p. 146–147° C. Anal. Calcd. for $C_{24}H_{16}SO_4Br_2$: C,51.43; H,2.86; S,5.71; Br,28.54, Found: C,51.13; H,2.56; S,5.78, Br,28.53.

Table 1 shows the relationship between reaction time and molar ratio (DBB/SDP) to the yield and weight ratio of the oligomer

TABLE 1

| Mole Ratio of DBB/SDP | Rxn. Time (Hrs.) | % Yield of BPDS & OBPDS | Weight Ratio of BPDS/OBPDS |
|---|---|---|---|
| 33/1 | 45 | 83 | 91/9 |
| 33/1 | 72 | 85 | 93/7 |
| 20/1 | 72 | 92 | 87/13 |
| 10/1 | 41 | 87 | 75/25 |
| 10/1 | 42 | 87 | 75/25 |
| 6/1 | 21 | 74 | 70/30 |
| 6/1 | 21 | 74 | 70/30 |
| 4/1 | 41 | 52 | 63/37 |
| 2/1 | 42 | 24 | 50/50 |
| 2/1 | 120 | 18 | 40/60 |
| 1.5/1 | 46 | 10 | 37/63 |

EXAMPLE 2

Conversion of BPDS/OBPDS to 4,4'-Bis(3-ethynyl-phenoxy)phenylsulfone and its Oligomers (ATS/OATS)

A mixture containing 81% BPDS and 19% OBPDS (23.0 g) was charged along with 2-methyl-3-butyn-2-ol (8.6 g), 150 ml triethylamine, and triphenylphosphine (0.25 g) to a 250 ml flask equipped with a thermometer, a magnetic stirrer, a nitrogen inlet-outlet and a condensor. A nitrogen atmosphere was established and bis(triphenylphosphine)palladium dichloride (50 mg) and cuprous iodide (50 mg) were added. The mixture was brought to reflux for 6 hours. The mixture was filtered and the filter cake washed with a little triethylamine. The filtrate and wash were stripped and the residue taken up in toluene (ca. 300 ml) and water (1×100 ml). Ethylenediamine (3 ml) was added and the solution brought to 60° C. for 30 minutes to complex traces of palladium. The solution was washed thoroughly with water. Analysis for atomic absorption at this point indicated less than 20 ppm of both Pd and Cu on a solvent-free basis. Several pellets of sodium hydroxide were added to the toluene solution, and the mixture was refluxed while removing acetone as it formed. When the formation of acetone ceased, the hot solution was treated with 2 g of charcoal and filtered through a layer of Celite. Stripping the solvent gave an orange oil (16.8 g, 91%). Gel permeation chromatography indicated 79% ATS and 21% OATS.

EXAMPLE 3

Preparation of 4,4'-bis(3-bromophenoxy)phenyl sulfide and 4,4'-bis(4-bromophenoxy)phenyl sulfide Using the procedure of Example 1, 4,4'-thiodiphenol (TDP) was reacted with the amount of dibromobenzene shown in Table 2. The mixture was stirred vigorously at 170° C. until the TLC analysis indicated the absence of both TDP and the monosubstituted phenol intermediate. The product was worked up as in Example 1. Table 2 shows the relationship between molar ratio (DBB:TDP) and reaction time to yield and the ratio of n=1 oligomer to n>1 oligomer.

TABLE 2

| DBB:TDP Ratio | Reaction Time (Hrs.) | Yield (%) | n = 1/n > 1 |
|---|---|---|---|
| 10:1a | 8 | 83 | 77/23 |
| 10:1b | 20 | 70 | 87/13 |
| 4:1a | 10 | 77 | 60/40 |
| 2:1a | 93 | 65 | 22/78 | a = 1,3-DBB
b = 1,4-DBB

EXAMPLE 4

Preparation of 2,2'-bis(4-[3-bromophenoxy]phenyl)propane and 2,2'-bis(4-[4-bromophenoxy]phenyl)propane Following the procedure in Example 3, dibromobenzene was reacted with Bisphenol A (BPA) in the mole ratios shown in Table 3 below. The reaction product was worked up as in Example 1. Analysis confirmed the presence of n=1 and n 1 oligomers. Table 3 illustrates the relation of DBB/BPA ratio and reaction times to yield and n=1/n>1 ratio.

TABLE 3

| DBB:BPA Ratio | Reaction Time (Hrs.) | Yield (%) | n = 1/n > 1 |
|---|---|---|---|
| 20:1a | 19.5 | 93 | 94/6 |
| 10:1a | 20.5 | 89 | 89/11 |
| 10:1b | 17.0 | 64 | 89/11 |
| 4:1a | 67 | 81 | 60/40 |
| 2:1a | 72 | 64 | 32/77 |
| 2:1b | 49 | 76 | 40/60 |

EXAMPLE 5

Preparation of 1,3-bis(bromophenoxy)benzene

The procedure set forth in Example 1 was followed except resorcinol (RES) was reacted with dibromobenzene (DBB) in the amounts shown in Table 4 below. The work-up was modified by using hexane in place of carbon tetrachloride. Analysis confirmed a mixture of n=1 and n>1 oligomers in the ratios shown.

TABLE 4

| DBB:RES Ratio | Reaction Time (Hrs.) | Yield (%) | n = 1/n > 1 |
|---|---|---|---|
| 10:1 | 30 | 80 | 92/8 |
| 2:1 | 21 | 49 | 45/55 |

What is claimed is:

1. A process for producing halogen-terminated oligomers useful in the production of acetylene-terminated oligomers which consists essentially of reacting a free aromatic diphenol selected from the group consisting of a sulfonyldiphenol, and alkylenediphenol, thiodiphenol and resorcinol with a dihalobenzene compound selected from the group consisting of 1,3-digromobenzene, 1,4-dibromobenzene, and mixtures thereof in the presence of at least a stoichiometric amount of cuprous oxide in an Ullman-type condensation in 2,4,6-collidine.

2. The process of claim 1 wherein said dihalobenzene compound is dibromobenzene.

3. The process of claim 1 wherein said diphenol is selected from the group consisting of 4,4'-sulfonyldiphenol, 4,4'-isopropylidenediphenol, 4,4'-thiophenol, and resorcinol.

4. The process of claim 3 wherein said diphenol is 4,4'-sulfonyldiphenol.

5. The process of claim 1 wherein, by varying the molar ratio of said dihalobenzene compound to said aromatic diphenol, the chain length of said oligomer can be adjusted.

6. The process of claim 1 wherein said diphenol is Bisphenol A.

* * * * *